United States Patent [19]

Dany et al.

[11] Patent Number: 5,427,755
[45] Date of Patent: Jun. 27, 1995

[54] PROCESS FOR THE PREPARATION OF A DICALCIUM PHOSPHATE DIHYDRATE SUITABLE FOR USE IN TOOTHPASTES

[75] Inventors: Franz-Josef Dany; Gerhard Kalteyer; Gerhard Nolte, all of Erftstadt; Hedwig Prell, Hürth, all of Germany

[73] Assignee: Hoechst Aktiengesellschaft, Frankfurt am Main, Germany

[21] Appl. No.: 197,952

[22] Filed: Feb. 17, 1994

[30] Foreign Application Priority Data

Mar. 4, 1993 [DE] Germany .................. 43 06 673.9

[51] Int. Cl.$^6$ ............................................. C01B 25/32
[52] U.S. Cl. ................................ 423/309; 423/265; 424/57
[58] Field of Search .................. 423/265, 308, 309; 424/57

[56] References Cited

U.S. PATENT DOCUMENTS

| | | | |
|---|---|---|---|
| 3,012,852 | 12/1961 | Nelson | 423/309 |
| 4,247,526 | 1/1981 | Jarvis et al. | 423/308 |
| 4,496,527 | 1/1985 | Sherif et al. | |
| 4,931,272 | 6/1990 | Dany et al. | 206/35 |

FOREIGN PATENT DOCUMENTS

| | | |
|---|---|---|
| 0045826 | 2/1982 | European Pat. Off. |
| 0240880 | 10/1987 | European Pat. Off. |
| 1548465 | 7/1979 | United Kingdom |

*Primary Examiner*—Wayne Langel
*Attorney, Agent, or Firm*—Connolly and Hutz

[57] ABSTRACT

In the process for the preparation of dicalcium phosphate dihydrate, which has a good compatibility with fluorine and stability to hydrolysis and causes the minimum possible after-thickening when used in toothpastes, by reaction of calcium carbonate suspended in water with an aqueous solution of orthophosphoric acid, precipitation of dimagnesium phosphate trihydrate, as a stabilizer, by reaction of aqueous solutions of a magnesium salt and of orthophosphoric acid in the presence of a basic compound and final filtration, drying and grinding of the precipitate, 0.2 to 0.8% by weight of polyphosphoric acid, calculated with respect to the dicalcium phosphate dihydrate precipitated in the reaction mixture, is added to the reaction mixture as a further stabilizer.

7 Claims, No Drawings

PROCESS FOR THE PREPARATION OF A DICALCIUM PHOSPHATE DIHYDRATE SUITABLE FOR USE IN TOOTHPASTES

The invention relates to a process for the preparation of dicalcium phosphate dihydrate, which has a good compatibility with fluorine and stability to hydrolysis and causes the minimum possible after-thickening when used in toothpastes, by reaction of calcium carbonate suspended in water with an aqueous solution of orthophosphoric acid in a first precipitating stage, precipitation of dimagnesium phosphate trihydrate, as a stabilizer, by reaction of aqueous solutions of a magnesium salt and of orthophosphoric acid in the presence of a basic compound in a second precipitating stage, and final filtering, drying and grinding of the precipitate.

Such a "short-term process" is essentially described in DE 26 48 061 C2 (=GB 1 548 465). Dicalcium phosphate dihydrate (DCP-D) and dimagnesium phosphate trihydrate (DMP-T) are also called calcium hydrogen phosphate dihydrate and magnesium hydrogen phosphate trihydrate respectively. The importance of the compatibility with fluorine and stability to hydrolysis is explained in DE 26 48 061 C2, column 2. The process of DE 26 48 061 C2 is not satisfactory in respect of the viscosity properties of the toothpastes prepared from the stabilized DCP-D. The after-thickening of the toothpastes which occurs with a DCP-D prepared in this way and is highly undesirable is caused, inter alia, by a loss of water of crystallization from the DCP-D and by its hydrolytic degradation to give calcium hydroxyapatite and orthophosphoric acid. At the same time, these undesirable reactions in fluorine-containing toothpastes cause a high loss of caries-prophylactic, active fluorine ions by intermediate formation of calcium fluoride and finally of fluoroapatite.

A process for the preparation of DCP-D is also known from DE 32 46 884 C2 (=U.S. Pat. No. 4,496,527), in which a slaked lime slurry is reacted with phosphoric acid to give a solution of DCP-D, to which is added such an amount of additional slaked lime slurry and pyrophosphoric acid that a DCP-D slurry having a pH of between 2.2 and 4.9 is obtained, and the resulting DCP-D is separated off from the slurry. The pyrophosphoric acid is added in an amount of 0.1 to 1.0% by weight, calculated with respect to the DCP-D to be prepared. Finished DMP-T can also be added as a stabilizer, for example to the reaction mash before the DCP-D is separated off.

However, the process of DE 32 46 884 C2 has the disadvantage that complete reaction of the slaked lime slurry with the phosphoric acids used requires at least 20 times the time of the short-term process described in DE 26 48 061 C2. Evidence that the reaction of the slaked lime slurry is incomplete in shorter reaction times can be provided by adding to a sample of the precipitation slurry a phenolphthalein solution, which indicates the unreacted calcium hydroxide particles as red points in the slurry.

The disadvantages of the prior art described can be largely avoided if 0.2 to 0.8% by weight of polyphosphoric acid, calculated with respect to the dicalcium phosphate dihydrate precipitated in the reaction mixture, is added to the reaction mixture, according to the present invention, as a further stabilizer in the short-term process described above.

The process according to the invention moreover preferably and optionally comprises a) employing polyphosphoric acid with a phosphorus content corresponding to 78% by weight of phosphorus pentoxide;

b) adding the polyphosphoric acid in the first precipitating stage towards the end of the precipitation of dicalcium phosphate dihydrate;

c) employing the polyphosphoric acid in the second precipitating stage as a mixture with the orthophosphoric acid;

d) employing the polyphosphoric acid in the second precipitating stage towards the end of the precipitation of dimagnesium phosphate trihydrate;

e) introducing approximately stoichiometric amounts of the calcium carbonate suspension and the orthophosphoric acid solution into a reaction vessel, keeping the reaction at temperatures which do not exceed 50° C. in a pH range of 2.2 to 2.6 and adding 0.2 to 0.8% by weight of polyphosphoric acid, calculated with respect to the dicalcium phosphate dihydrate precipitated in the reaction mixture, towards the end of the reaction; increasing the pH of the reaction mixture to 5.6 to 5.8 with sodium hydroxide solution, precipitating dimagnesium phosphate trihydrate in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid and sodium hydroxide solution, bringing the pH to the neutral point with sodium hydroxide solution and subsequently stirring the reaction mixture for 2 to 3 minutes; and separating off the precipitated product from the reaction mixture, drying it and comminuting it to the particle size customary for use in toothpastes.

f) introducing approximately stoichiometric amounts of the calcium carbonate suspension and the orthophosphoric acid solution into a reaction vessel and keeping the reaction at temperatures which do not exceed 50° C. in a pH range of 2.2 to 2.6; increasing the pH of the reaction mixture to 5.6 to 5.8 with sodium hydroxide solution and precipitating dimagnesium phosphate trihydrate in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid mixed with 0.2 to 0.8% by weight of polyphosphoric acid, calculated with respect to the dicalcium phosphate dihydrate precipitated in the reaction mixture, and sodium hydroxide solution, bringing the pH to the neutral point with sodium hydroxide solution and subsequently stirring the reaction mixture for 2 to 3 minutes; and separating off the precipitated product from the reaction mixture, drying it and comminuting it to the particle size customary for use in toothpastes;

g) introducing approximately stoichiometric amounts of the calcium carbonate suspension and the orthophosphoric acid solution into a reaction vessel and keeping the reaction at temperatures which do not exceed 50° C. in a pH range of 2.2 to 2.6; increasing the pH range of the reaction mixture to 5.6 to 5.8 with sodium hydroxide solution and precipitating dimagnesium phosphate trihydrate in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid and sodium hydroxide solution; adding 0.2 to 0.8% by weight of polyphosphoric acid, calculated with respect to the dicalcium phosphate dihydrate precipitated in the reaction mixture, towards the end of this precipitation, subsequently stirring the reaction mixture for 2 to 3 minutes and simultaneously bringing the pH to the neutral point with sodium hydroxide solution; and separating off the precipitated product from the reaction mixture, drying it and comminuting it to the particle size customary for use in toothpastes;

h) reducing the stoichiometric amount of orthophosphoric acid to be introduced in the second precipitating stage according to the equivalent acidity of the amount of polyphosphoric acid to be added; and i) providing the reaction vessel with a double jacket for the purpose of cooling.

Magnesium chloride or nitrate, for example, can be employed as the magnesium salt.

The following examples are intended to illustrate the process according to the invention for the preparation and stabilization of DCP-D.

EXAMPLE 1

(for comparison)

2 kg of water were initially introduced into a stirrable stainless steel reactor provided with a double jacket for the purpose of cooling (in order to limit the reaction temperature to a maximum of 50° C.). 1 kg of calcium carbonate as a 40% strength by weight aqueous suspension and a mixture of 0.9791 kg of orthophosphoric acid as a 75% strength by weight aqueous solution and 6.88 g of polyphosphoric acid (78% by weight of phosphorus pentoxide) were then introduced simultaneously, while stirring by means of a propeller (1300 revolutions per minute), in a manner such that the pH of the reaction mixture was kept in the range from 2.2 to 2.6. The pH was then increased to 5.7 by addition of 25% strength by weight sodium hydroxide solution. The pH was then controlled such that it did not exceed a value of 6 by simultaneous introduction of 0.0235 kg of magnesium chloride as a 33.3% strength by weight aqueous solution, 0.0242 kg of orthophosphoric acid as a 75% strength by weight aqueous solution and 25% strength by weight sodium hydroxide solution. The reaction mixture was subsequently stirred for 2 to 3 minutes and the pH was increased to the neutral point by further addition of sodium hydroxide solution. The precipitate formed was filtered off over a porcelain suction filter, washed with a copious amount of distilled water, dried and comminuted to the particle size necessary for use in toothpastes.

The amount of DMP-T precipitated was 0.043 kg, corresponding to 2.5% by weight, and the amount of polyphosphoric acid (78% by weight of $P_2O_5$s) introduced was 0.4% by weight, in each case calculated with respect to 1.7194 kg of precipitated DCP-D.

EXAMPLE 2

As Example 1, with the difference that the 6.88 g of polyphosphoric acid (78% by weight of $P_2O_5$) was not added to the orthophosphoric acid but was added separately at a pH of 2.2 to 2.6 after the reaction between the calcium carbonate and the orthophosphoric acid had practically ended. After the pH had then been raised to 5.7, the subsequent procedure was as in Example 1.

EXAMPLE 3

As Example 1, with the difference that the 6.88 g of polyphosphoric acid were mixed with the 0.0242 kg of orthophosphoric acid required for the second precipitating stage and reacted with 0.0235 kg of magnesium chloride as a 33.3% strength by weight aqueous solution, while simultaneously adding 25% strength by weight sodium hydroxide solution. In this case, the reaction was controlled by appropriate metering of the sodium hydroxide solution such that the pH of 6 was not exceeded. After the mixture had been subsequently stirred for 2 to 3 minutes, the pH was increased to the neutral point by means of sodium hydroxide solution.

EXAMPLE 4

As Example 1, with the difference that the 6.88 g of polyphosphoric acid were added separately at the end of the second precipitating step. In this case, the content of orthophosphoric acid was reduced to 0.02343 kg and was added to the reaction mixture with 0.0235 kg of magnesium chloride, with simultaneous addition of sodium hydroxide solution, in a manner such that the pH of 6 was not exceeded. 6.88 g of polyphosphoric acid were then added separately, while simultaneously metering in sodium hydroxide solution, at a pH of less than 6. After the mixture had been subsequently stirred for 2 to 3 minutes, the pH was brought to the neutral point by means of sodium hydroxide solution.

EXAMPLE 5

As Example 4, with the difference that the orthophosphoric acid required for the second precipitating step was reduced to 0.02382 kg and the amount of polyphosphoric acid added separately was 3.44 g.

The amount of polyphosphoric acid introduced (3.44 g) was 0.2% by weight, calculated with respect to the DCP-D precipitated.

EXAMPLE 6

As Example 4, with the difference that the amount of orthophosphoric acid was 0.02304 kg and the amount of polyphosphoric acid was 10.3 g.

The amount of polyphosphoric acid introduced (10.3 g) was 0.6% by weight, calculated with respect to the DCP-D precipitated.

EXAMPLE 7

As Example 4, with the difference that the amount of orthophosphoric acid was 0.02266 kg and the amount of polyphosphoric acid was 13.8 g.

The amount of polyphosphoric acid introduced (13.8 g) was 0.8% by weight, calculated with respect to the DCP-D precipitated.

The products prepared according to Examples 1 to 7 were investigated in respect of their stability properties.

The compatibility of the individual products with fluorine was tested by the following method:

10 g of the DCP-D to be tested are suspended in 90 g of water and the suspension is heated to 80° C. 76 mg of sodium monofluorophosphate ($Na_2FPO_3$, corresponding to 1000 ppm of fluorine, based on the DCP-D employed) are then introduced. The suspension is kept at 80° C. for exactly 1 hour, while stirring continuously. It is cooled to room temperature in an ice-bath and filtered over a frit, and the fluorine content is determined in an aliquot portion of the filtrate.

The content of soluble fluorine ion is a measure of the compatibility of the DCP-D with fluorine. This is stated in % by weight of the starting value.

The following method was used for determination of the stability to hydrolysis:

25 g of the DCP-D to be tested are suspended in a solution of 1.63 g of sodium fluoride in 100 ml of water, which is heated at 60° C. and kept at this temperature, and are kept in suspension by means of a stirrer. During this procedure, the pH is recorded continuously. The time at which the pH falls below 4 is determined. The time taken to reach pH=4 is a measure of the stability of the DCP-D to hydrolysis.

The paste viscosity properties were investigated in the following manner:

Toothpastes based on the following formulation were prepared from the individual DCP-D products according to Examples 1 to 7:
48.0 parts by weight of DCP-D
24.0 parts by weight of sorbitol (70% strength by weight aqueous solution)
6.0 parts by weight of glycerol
1.5 parts by weight of sodium lauryl sulfate
0.8 part by weight of binder
0.8 part by weight of flavoring
0.76 part by weight of sodium monofluorophosphate
0.25 part by weight of tetrasodium diphosphate
0.2 part by weight of sodium saccharinate
to 100 parts by weight with deionized water.

Aluminum tubes were filled with the pastes prepared on the basis of the above recipe and were kept at 25° C. for 24 hours. The viscosity was measured in scale divisions (s.d.) by means of a rotary viscometer (Brookfield RVT DV II spindle D) at the ambient temperature. The pastes were then stored at 49° C., the viscosity measurement being repeated after 3 and after 9 weeks, after cooling to the ambient temperature.

For better clarity, the stability and viscosity results of the pastes prepared from the individual DCP-D products of Examples 1 to 7 are summarized in tabular form below, the preparation method being stated:

| Example No. | 1 | 2 | 3 | 4 | 5 | 6 | 7 |
|---|---|---|---|---|---|---|---|
| $MgHPO_4 \cdot 3H_2O$ (% by wt.) | 2.5 | 2.5 | 2.5 | 2.5 | 2.5 | 2.5 | 2.5 |
| Polyphosphoric acid (% by wt.) | 0.4 | 0.4 | 0.4 | 0.4 | 0.2 | 0.6 | 0.8 |
| Type of stabilization*) | A | B | C | D | D | D | D |
| Compatibility with fluorine (% by wt. of water-soluble fluorine) | 76 | 77 | 80 | 82 | 80 | 83 | 83 |
| Stability to hydrolysis (time (h) to reach pH = 4) | 9.6 | 10.2 | 12.3 | >20 | 19.3 | >20 | >20 |
| Paste viscosity (scale divisions) | | | | | | | |
| after 24 h at 25° C. | 23 | 24 | 24 | 24 | 22 | 25 | 26 |
| after 3 weeks at 49° C. | 70 | 69 | 70 | 34 | 36 | 36 | 37 |
| after 9 weeks at 49° C. | 87 | 78 | 74 | 45 | 48 | 47 | 49 |

*)A: Addition of the polyphosphoric acid as a mixture with the orthophosphoric acid required for the first precipitating stage.
B: Separate addition of the polyphosphoric acid, after the reaction of calcium carbonate with orthophosphoric acid has practically ended, at a pH of 2.2 to 2.6.
C: Addition of the polyphosphoric acid as a mixture with the orthophosphoric acid required for the second precipitating stage.
D: Separate addition of the polyphosphoric acid at the end of the second precipitating stage, after the amount of orthophosphoric acid has been reduced by the equivalent acidity of the polyphosphoric acid.

As can be seen the products according to the invention, which are prepared according to Example 4 to 7 (stabilization D), give by far the best results with respect to the viscosity properties of the toothpastes prepared therefrom, good values for the compatibility with fluorine and stability to hydrolysis also being found at the same time.

We claim:
1. In a process for the preparation of dicalcium phosphate dihydrate, which has a good compatibility with fluorine and stability to hydrolysis and causes the minimum possible after-thickening when used in toothpastes, by reaction in a reaction vessel of calcium carbonate suspended in water with an aqueous solution of orthophosphoric acid in a first precipitating stage, precipitation of dimagnesium phosphate trihydrate, as a stabilizer, by reaction of aqueous solutions of a magnesium salt and of orthophosphoric acid in the presence of a basic compound in a second precipitating stage and final filtering, drying and grinding of the precipitate, the improvement which comprises adding 0.2 to 0.8% by weight of polyphosphoric acid, calculated with respect to the dicalcium phosphate dihydrate precipitated, as a further stabilizer
   a) in the first precipitating stage in a pH-range from 2.2 to 2.6 towards the end of the precipitation of dicalcium phosphate dihydrate; or
   b) in the second precipitating stage as a mixture with the orthophosphoric acid at a pH of 5.6 to 6.0; or
   c) in the second precipitating stage at a pH of 5.6 to 6.0 towards the end of the precipitation of dimagnesium phosphate trihydrate.

2. A process as claimed in claim 1, wherein polyphosphoric acid with a phosphorus content corresponding to 78% by weight of phosphorus pentoxide is employed.

3. A process as claimed in claim 1 wherein approximately stoichiometric amounts of the calcium carbonate suspension and the orthophosphoric acid solution are introduced into the reaction vessel, the reaction is kept at temperatures which do not exceed 50° C. in a pH range from 2.2 to 2.6 and 0.2 to 0.8% by weight of polyphosphoric acid, calculated with respect to the dicalcium phosphate dihydrate precipitated in the reaction mixture, is added towards the end of the reaction; wherein the pH of the reaction mixture is increased to 5.6 to 5.8 with sodium hydroxide solution and dimagnesium phosphate trihydrate is precipitated in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid and sodium hydroxide solution, the pH is brought to the neutral point with sodium hydroxide solution and the reaction mixture is subsequently stirred for 2 to 3 minutes; and wherein the precipitated product is separated off from the reaction mixture, dried and comminuted.

4. A process as claimed in claim 1, wherein approximately stoichiometric amounts of the calcium carbonate suspension and the orthophosphoric acid solution are introduced into the reaction vessel and the reaction is kept at temperatures which do not exceed 50° C. in a pH range from 2.2 to 2.6; wherein the pH of the reaction mixture is increased to 5.6 to 5.8 with sodium hydroxide solution and dimagnesium phosphate trihydrate is precipitated in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid mixed with 0.2 to 0.8% by weight of polyphosphoric acid, calculated with respect to the dicalcium phosphate dihydrate precipitated in the reaction mixture, and sodium hydroxide solution, the pH is brought to the neutral point with sodium hydroxide solution and the reaction mixture is subsequently stirred for 2 to 3 minutes; and wherein the precipitated product is separated off from the reaction mixture, dried and comminuted.

5. A process as claimed in claim 1, wherein approximately stoichiometric amounts of the calcium carbonate suspension and the orthophosphoric acid solution are introduced into the reaction vessel and the reaction is kept at temperatures which do not exceed 50° C. in a pH range from 2.2 to 2.6; wherein the pH of the reaction mixture is increased to 5.6 to 5.8 with sodium hydroxide solution and dimagnesium phosphate trihydrate is precipitated in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid and sodium hydroxide solution; wherein 0.2 to 0.8% by weight of polyphosphoric acid, calculated with respect to the dicalcium phosphate dihydrate precipitated in the reaction mixture, is added to the reaction mixture towards the end of this precipitation, the reaction mixture is subsequently stirred for 2 to 3 minutes and the pH is simultaneously brought to the neutral point with sodium hydroxide solution; and wherein the precipitated product is separated off from the reaction mixture, dried and comminuted.

6. A process as claimed in claim 5, wherein the stoichiometric amount of orthophosphoric acid to be introduced in the second precipitating stage is reduced in accordance with the equivalent acidity of the amount of polyphosphoric acid to be added.

7. A process as claimed in claim 1, wherein the reaction vessel is provided with a double jacket for the purpose of cooling.

* * * * *